US012601378B2

(12) United States Patent
Lehrke

(10) Patent No.: US 12,601,378 B2
(45) Date of Patent: Apr. 14, 2026

(54) QUICK CONNECT MECHANISM FOR MOUNTING OF MEDICAL INSTRUMENTS

(71) Applicant: Acist Medical Systems, Inc., Eden Prairie, MN (US)

(72) Inventor: Jacob Ryan Lehrke, Eden Prairie, MN (US)

( * ) Notice: Subject to any disclaimer, the term of this patent is extended or adjusted under 35 U.S.C. 154(b) by 438 days.

(21) Appl. No.: 18/339,589

(22) Filed: Jun. 22, 2023

(65) Prior Publication Data

US 2024/0426347 A1 Dec. 26, 2024

(51) Int. Cl.
*F16D 1/10* (2006.01)
*A61B 50/20* (2016.01)

(52) U.S. Cl.
CPC .............. *F16D 1/101* (2013.01); *A61B 50/20* (2016.02); *F16D 2001/103* (2013.01); *Y10T 403/559* (2015.01); *Y10T 403/7045* (2015.01)

(58) Field of Classification Search
CPC .......... F16D 1/101; F16D 1/104; F16D 1/108; F16D 1/112; F16D 1/116; F16D 2001/102; F16D 2001/103; Y10T 403/559; Y10T 403/7026; Y10T 403/7045; A61B 50/20; A61B 50/24; A61B 2017/0046; A61B 2017/00477
See application file for complete search history.

(56) References Cited

U.S. PATENT DOCUMENTS

| | | | | | |
|---|---|---|---|---|---|
| 548,221 | A | * | 10/1895 | Rastetter | E04B 1/2604 |
| | | | | | 74/552 |
| 558,470 | A | * | 4/1896 | Berkey | B60B 21/06 |
| | | | | | 301/58 |

| | | | | | |
|---|---|---|---|---|---|
| 776,391 | A | * | 11/1904 | Giese | E21B 17/043 |
| | | | | | 403/364 |
| 1,260,690 | A | * | 3/1918 | Liady | F16L 13/141 |
| | | | | | 403/364 |
| 1,781,091 | A | * | 11/1930 | Wilson | E21B 17/046 |
| | | | | | 285/333 |
| 3,741,251 | A | | 6/1973 | Rees | |
| 3,880,267 | A | * | 4/1975 | Auble | F16D 11/14 |
| | | | | | 192/55.2 |

(Continued)

FOREIGN PATENT DOCUMENTS

| | | | |
|---|---|---|---|
| CN | 207935307 U | 10/2018 | |
| EP | 0132355 B1 | 3/1988 | |

(Continued)

OTHER PUBLICATIONS

Patent Cooperation Treaty, "International Search Report and Written Opinion," PCT/IB2024/056097, Sep. 13, 2024, 9 pages.

*Primary Examiner* — Amber R Anderson
*Assistant Examiner* — Kevin J Baynes
(74) *Attorney, Agent, or Firm* — Carlson, Caspers, Vandenburgh & Lindquist, P.A.

(57) ABSTRACT

A quick connect mechanism for a medical instrument is provided. The quick connect mechanism includes a post and a mating cup that allows for quick mounting, controlled use, and easy dismounting of medical instruments. A set of post teeth are disposed circumferentially around a body proximate a base of the post and are configured to mate and interlock with a set of cup teeth disposed proximate the cup. The post teeth and cup teeth interlock to restrict rotation of the cup relative to the post and stabilize the medical instrument.

22 Claims, 6 Drawing Sheets

(56)                References Cited

U.S. PATENT DOCUMENTS

| | | | | |
|---|---|---|---|---|
| 4,435,104 | A * | 3/1984 | Held | E06B 3/984 |
| | | | | 403/364 |
| 4,512,596 | A * | 4/1985 | Obrecht | F16D 1/02 |
| | | | | 285/330 |
| 4,578,608 | A * | 3/1986 | Mech | H02K 5/132 |
| | | | | 403/364 |
| 4,792,320 | A * | 12/1988 | Nickel | F16C 3/026 |
| | | | | 464/181 |
| 5,001,824 | A * | 3/1991 | Ayers | F16D 1/033 |
| | | | | 464/79 |
| 5,269,572 | A * | 12/1993 | Mefferd | F16L 21/06 |
| | | | | 403/339 |
| 5,730,657 | A * | 3/1998 | Olgren | F16D 3/18 |
| | | | | 464/157 |
| 6,352,385 | B1 * | 3/2002 | Wojciechowski | F16D 1/033 |
| | | | | 403/364 |
| 6,375,577 | B1 * | 4/2002 | Smith | F16D 3/66 |
| | | | | 464/106 |
| 6,547,479 | B2 | 4/2003 | Dowling, Jr. et al. | |
| 6,604,885 | B1 | 8/2003 | Neuner | |
| 7,387,269 | B2 | 6/2008 | Mally | |
| 7,762,185 | B2 | 7/2010 | Machaj et al. | |
| 8,161,619 | B2 * | 4/2012 | Wanthal | B64C 1/06 |
| | | | | 464/181 |
| 8,313,067 | B2 * | 11/2012 | Knieriem | F16M 11/42 |
| | | | | 248/188.7 |
| 8,465,373 | B2 * | 6/2013 | Dornfeld | F16D 1/076 |
| | | | | 464/157 |
| 8,739,861 | B2 * | 6/2014 | Hughes | E21B 17/046 |
| | | | | 166/380 |
| 9,757,129 | B2 * | 9/2017 | Williams | A61B 17/07207 |
| 9,845,645 | B2 * | 12/2017 | Hughes | E21B 17/042 |
| 10,046,737 | B2 | 8/2018 | Wozniak et al. | |
| 10,060,197 | B2 | 8/2018 | Hughes et al. | |
| 10,299,803 | B2 * | 5/2019 | Inamdar | A61B 17/162 |
| 10,443,647 | B2 * | 10/2019 | Itagaki | F16C 3/02 |
| 11,337,372 | B2 | 5/2022 | Hullebusch et al. | |
| 11,859,649 | B2 * | 1/2024 | Emil | A61B 17/56 |
| 12,215,745 | B1 * | 2/2025 | Carlson | F16D 25/062 |
| 2004/0267254 | A1 * | 12/2004 | Manzo | A61B 18/14 |
| | | | | 606/49 |
| 2008/0086150 | A1 * | 4/2008 | Mathis | A61B 34/20 |
| | | | | 606/130 |
| 2008/0230218 | A1 * | 9/2008 | Hall | E21B 17/046 |
| | | | | 166/242.2 |
| 2014/0050522 | A1 * | 2/2014 | Slaughter, Jr. | E21B 17/03 |
| | | | | 403/342 |
| 2020/0306845 | A1 * | 10/2020 | Kimura | F16D 1/101 |
| 2021/0322081 | A1 * | 10/2021 | Sweitzer | A61F 2/4603 |
| 2023/0036742 | A1 | 2/2023 | McKenney et al. | |
| 2023/0053518 | A1 * | 2/2023 | Ibrahim | B60T 13/745 |

FOREIGN PATENT DOCUMENTS

| | | | | | |
|---|---|---|---|---|---|
| EP | 3169865 | B1 | 11/2020 | | |
| FR | 2990253 | A1 * | 11/2013 | | B60B 35/12 |
| FR | 3068741 | A1 * | 1/2019 | | F04D 17/12 |
| JP | 2002340005 | A | 11/2002 | | |
| WO | WO-2018196419 | A1 * | 11/2018 | | F04D 29/054 |
| WO | 2023284507 | A1 | 1/2023 | | |

* cited by examiner

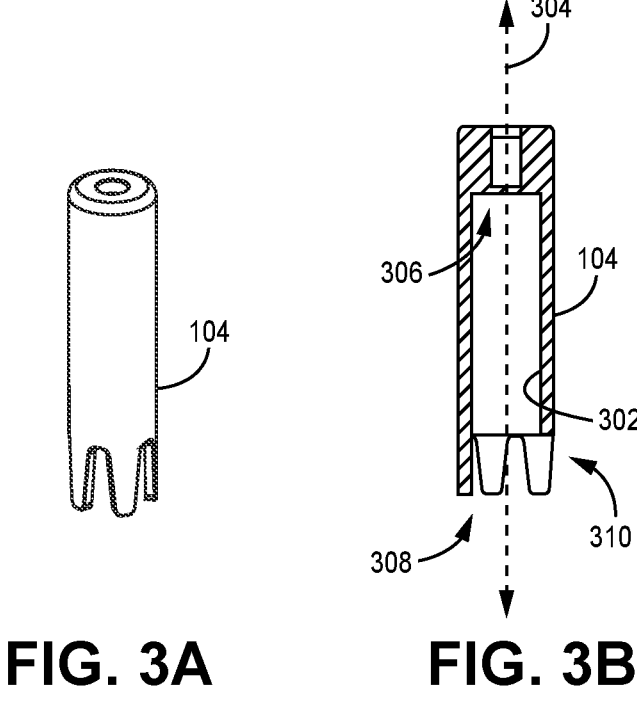
FIG. 3A          FIG. 3B
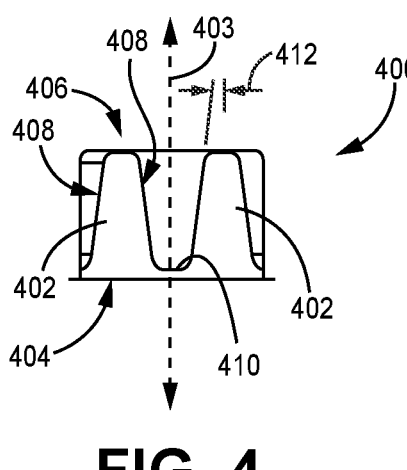
FIG. 4

FIG. 6A                    FIG. 6B

QUICK CONNECT MECHANISM FOR MOUNTING OF MEDICAL INSTRUMENTS

BACKGROUND

Many medical instruments are brought into the space where the patient is present in order to be used in connection with that patient. Often these medical instruments are requested to be used in tight subsequent phases of a given medical procedure that the patient is subjected to. Moreover, since the operating rooms and the cardiac catheterization labs are typically quite narrow environments, a medical equipment needs to be located close to the patient and then quickly moved away from the patient so as to leave space to a different medical equipment to perform a successive step of the medical procedure. Larger medical instruments often have their own cart with wheels to wheel the instrument into the space and support the instrument while it is being used.

SUMMARY

The subject matter described herein includes a quick connect mechanism for a medical instrument. In Example 1, the quick connect mechanism includes a post body and a cup. The post body defines a post having an elongated geometry with a round cross-section that defines a post axis about its center. The post has a distal end. The post body also defines a set of post teeth disposed circumferentially about the post axis. Each tooth in the set of post teeth extends in parallel with the post axis towards the distal end of the post, each tooth in the set of post teeth having lateral edges that define gaps between adjacent teeth. The lateral edges are angled relative to the post axis such that a distal end of each tooth is narrower than a base of the tooth. The cup of the quick connect mechanism defines a recess having an elongated geometry with a round cross-section that defines a recess axis about its center. The recess has an inner end and an outer end. The cup also defines a set of cup teeth disposed circumferentially about the recess axis. Each tooth in the set of cup teeth extends in parallel with the recess axis. Each tooth in the set of cup teeth has lateral edges that define gaps between adjacent teeth. The lateral edges are angled relative to the recess axis such that a distal end of each tooth is narrower than a base of the tooth. One of the post body or the cup is configured to be mounted such that the post axis or recess axis respectively is disposed vertically and the other of the post body or cup is disposed on the medical instrument. The recess is configured to mate with the post such that the post axis is aligned with the recess axis and an outer surface of the post maintains contact with an inner surface of the recess in order to mount the medical instrument to the post body. The set of cup teeth are configured to mate with the set of post teeth in order to restrict rotation of the cup relative to the post about the recess axis.

Example 2 includes the quick connect mechanism of Example 1, wherein the set of post teeth and the set of cup teeth have dimensions such that the lateral edges of the set of post teeth maintain contact with the lateral edges of the set of cup teeth while mated.

Example 3 includes the quick connect mechanism of any of Examples 1 or 2, wherein the lateral edges of the set of post teeth are angled relative to the post axis in the same manner as the lateral edges of the set of cup teeth are angled relative to the recess axis to provide an elongated contact surface between the lateral edges of the set of post teeth and the lateral edges of the set of cup teeth.

Example 4 includes the quick connect mechanism of any of Examples 1-3, wherein a distal end of the post teeth is spaced apart from the gap between cup teeth and a distal end of the cup teeth is spaced apart from the gap between post teeth while mated.

Example 5 includes the quick connect mechanism of any of Examples 1-4, wherein the post has a length that is at least 1.5 times longer than its diameter and the recess has a length that is at least 1.5 times longer than its diameter.

Example 6 includes the quick connect mechanism of any of Examples 1-5, wherein an outer surface of the post is smooth and an inner surface of the recess is smooth to allow the outer surface of the post to slide against the inner surface of the recess during insertion of the post into the recess.

Example 7 includes the quick connect mechanism of any of Examples 1-6, wherein the set of post teeth are disposed proximate the base of the post and the set of cup teeth are disposed proximate the outer end of the recess.

Example 8 includes the quick connect mechanism of any of Examples 1-7, wherein the set of post teeth and the set of cup teeth each include at least three teeth.

Example 9 includes the quick connect mechanism of any of Examples 1-8, wherein the lateral edges of the set of post teeth are angled less than 30 degrees off the post axis and the lateral edges of the set of cup teeth are angled less than 30 degrees off the recess axis.

Example 10 includes the quick connect mechanism of any of Examples 1-9, wherein a diameter defined by the inner surface of the recess is less than 1 mm larger a diameter defined by the outer surface of the post.

Example 11 includes the quick connect mechanism of any of Examples 1-10, including a torque controller having a body and an arm and being configured to control rotation of the arm relative to the body about a torque axis, wherein the body of the torque controller is mounted to the medical instrument in a fixed relationship and the arm of the torque controller is mounted to the cup in a fixed relationship, wherein the torque axis is aligned with the recess axis of the cup.

Example 12 includes a quick connect mechanism for a medical instrument. The mechanism includes a post body and a cup. The post body includes a post having an outer surface that is smooth and forms a cylinder. The post defies a post cylindrical axis about a center of the cylinder. The post has a base and a distal end. The post body also includes a set of post teeth disposed proximate the base of the post and disposed circumferentially about the post cylindrical axis. An outer surface of the set of post teeth defines a diameter that is larger than a diameter of the cylinder formed by the outer surface of the post. Each tooth in the set of post teeth extends in parallel with the post cylindrical axis towards the distal end of the post. Each tooth in the set of post teeth has lateral edges that define gaps between adjacent teeth. The lateral edges are angled relative to the post cylindrical axis such that a distal end of each tooth is narrower than a base of the tooth. The cup of the quick connect mechanism defines a recess having an inner surface that is smooth and forms a cylinder. The recess defines a recess cylindrical axis about a center of the cylinder. The recess has an inner end and an outer end. The cup of the quick connect mechanism also defines a set of cup teeth extending from the outer end of the recess and disposed circumferentially about the recess cylindrical axis. An inner surface of the set of cup teeth defines a diameter that is larger than the diameter of the cylinder formed by the outer surface of the post and smaller than the diameter formed by the outer surface of the set of post teeth. Each tooth in the set of cup teeth extends in parallel with the recess cylindrical axis away from the outer end of the recess. Each tooth in the set of cup teeth has lateral edges that define gaps between adjacent teeth. The lateral edges are angled relative to the recess cylindrical axis such that a distal end of each tooth is narrower than a base of the tooth. The post body is configured to be mounted such that the post cylindrical axis is disposed vertically and the cup is disposed on a medical instrument. The recess is configured to mate with the post such that the post cylindrical axis is aligned with the recess cylindrical axis and the outer surface of the post maintains contact with the inner surface of the recess in order to mount the medical instrument to the post body. The set of cup teeth are configured to mate with the set of post teeth in order to restrict rotation of the cup relative to the post about the post cylindrical axis.

Example 13 includes the quick connect mechanism of Example 12, wherein the set of post teeth and the set of cup teeth have dimensions such that the lateral edges of the set of post teeth maintain contact with the lateral edges of the set of cup teeth while mated.

Example 14 includes the quick connect mechanism of any of Examples 12 or 13, wherein the lateral edges of the set of post teeth are angled relative to the post cylindrical axis in the same manner as the lateral edges of the set of cup teeth are angled relative to the recess cylindrical axis to provide an elongated contact surface between the lateral edges of the set of post teeth and the lateral edges of the set of cup teeth.

Example 15 includes the quick connect mechanism of any of Examples 12-14, wherein a distal end of the post teeth is spaced apart from the gap between cup teeth and a distal end of the cup teeth is spaced apart from the gap between post teeth while mated.

Example 16 includes the quick connect mechanism of any of Examples 12-15, wherein the post has a length that is at least 1.5 times longer than its diameter and the recess has a length that is at least 1.5 times longer than its diameter.

Example 17 includes the quick connect mechanism of any of Examples 12-16, wherein a diameter defined by the inner surface of the recess is less than 1 mm larger a diameter defined by the outer surface of the post.

Example 18 includes the quick connect mechanism of any of Examples 12-17, wherein the set of post teeth and the set of cup teeth each include at least three teeth.

Example 19 includes the quick connect mechanism of any of Examples 12-18, wherein the lateral edges of the set of post teeth are angled less than 15 degrees off the post cylindrical axis and the lateral edges of the set of cup teeth are angled less than 15 degrees off the recess cylindrical axis.

Example 20 includes the quick connect mechanism of any of Examples 12-19, including a torque controller having a body and an arm and being configured to control rotation of the arm relative to the body about a torque axis, wherein the body of the torque controller is mounted to the medical instrument in a fixed relationship and the arm of the torque controller is mounted to the cup in a fixed relationship, wherein the torque axis is aligned with the recess cylindrical axis.

BRIEF DESCRIPTION OF THE DRAWINGS

FIGS. 3A and 3B are a perspective view and a cross-sectional view, respectively, of an example cup of the quick connect mechanism of FIG. 1;

FIG. 4 is an enlarged perspective view of example teeth that can be used on the post body and cup of FIGS. 2, 3A, and 3B;

DETAILED DESCRIPTION

The subject matter described herein provides for a quick connect mechanism that allows quick mounting, controlled use, and easy dismounting of medical instruments. By way of example, a medical instrument may be fitted with a cup that mates with a post, the post being fixed to the patient bedside such that the instrument can be mounted and dismounted from the patient's bed by setting the instrument onto the post, thereby mating the cup and post, and can be disconnected by lifting the instrument off of the post. The configuration of the quick connect mechanism described herein enables such easily mounting and dismounting while still providing stability for the medical instrument while it is mounted and operated by the technical personnel (e.g., physicians, nurses, technical operators).

Figure 1:
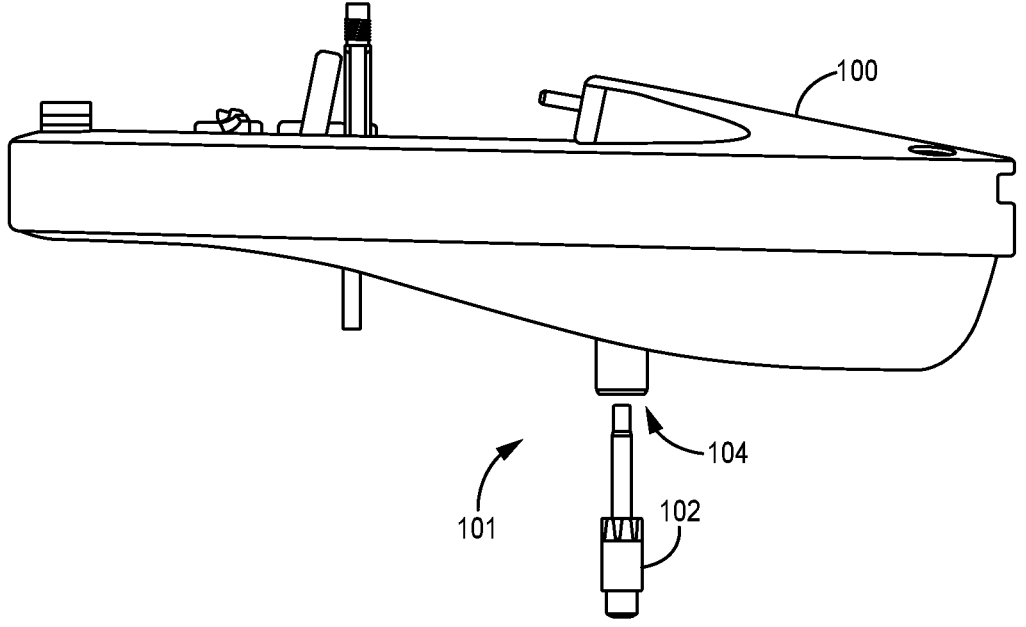
FIG. 1 is a perspective view of an example quick connect mechanism used with a medical instrument.

FIG. 1 is a perspective view of an example medical instrument 100 that is equipped with a quick connect mechanism 101 as described herein. The quick connect mechanism 101 includes a post body 102 and a cup 104 that are configured to mate together to enable the medical instrument 100 to be mounted and dismounted without tools. In this example, the cup 104 is integrated into the medical instrument 100 and the post body 102 is configured to be disposed in a location in which it is desired to mount the medical instrument 100. For example, the post body 102 can be mounted or otherwise fixed to a patient's bed (e.g., to a bedrail), to a wall, to a cart, to a ceiling mount, or to other furniture or supports nearby the patient, if that is a desired location to mount the medical instrument 100. The post body 102 can be fixed to such a supporting element in any suitable manner such as with one or more clamps, rigid or articulating arms, or the like. The post body 102 is configured to be disposed and maintained in a vertical orientation such that a post of the post body 102 preferably points upward during use as described in more detail below.

The cup 104 is integrated with or otherwise attached to the medical instrument 100 and defines a recess that is configured to mate with the post of the post body 102, such that the medical instrument 100 can be mounted onto the post body 102 via manual manipulation by a user. According to the embodiment shown in the figures, the medical instrument 100 can be mounted by positioning the recess of the cup 104 over the post of the post body 102 and sliding the recess of the cup 104 onto the post of the post body 102. When fully engaged, the post of the post body 102 is disposed within the recess of the cup 104 and the user no longer needs to hold the medical instrument 100. The post body 102 is configured to support the weight of the medical instrument 100 and contact between the cup 104 and the post body 102 provides stability for the medical instrument 100 (e.g., prevents the medical instrument 100 from tipping or otherwise falling off the post). Thus, a user can easily and quickly mount the medical instrument 100. Once the medical instrument 100 is mounted it will be held in place by the post body 102 and the cup 104 in a hands-free manner (i.e., without need for the user to hold or otherwise manually stabilize the instrument 100). The cup 104 can be integrated into the medical instrument 100 in any suitable manner including as an add-on component or as an OEM component. The cup 104 can be disposed such that the recess opens downwards when the medical instrument 100 is in use, which positions the medical instrument 100 in the proper orientation while the cup 104 is mounted onto a vertically (upwards) oriented post of the post body 102. While it is not a requirement, the cup 104 can be disposed such that the recess is near the center-of-gravity of the medical instrument 100 to provide more even weight distribution on the post of the post body 102. To remove the medical instrument 100, a user can manually lift the medical instrument 100 off the post of the post body 102. Once the recess of the cup 104 is clear of the post from the post body 102, the medical instrument 100 is freely maneuverable and can be carried or otherwise moved away as desired.

Figure 2:
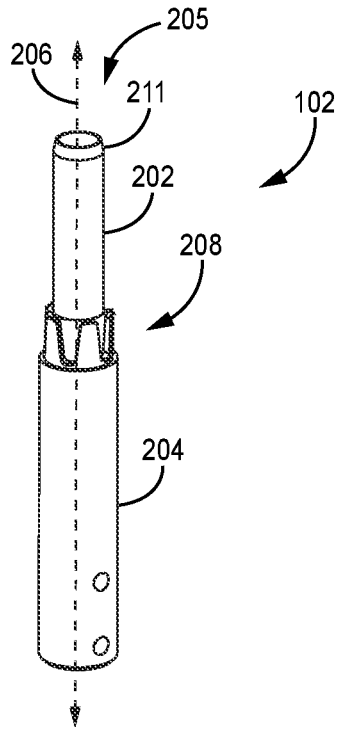
FIG. 2 is a perspective view of a portion of an example post body of the quick connect mechanism of FIG. 1.

FIG. 2 is a perspective view of an example post body 102 suitable for use in the quick connect mechanism 101 described with respect to FIG. 1. The post body 102 includes a post 202 that extends from a base 204. The base 204 is fixed or otherwise mounted to a supporting element in a desired location, such as a patient's bed (e.g., to a bedrail), to a wall, to a cart, to a ceiling mount, or to other furniture or supports as described above. The base 204 can also be an integral part of the supporting element it is fixed to, such as being an integral part of the bedrail. The post 202 extends from the base 204, defines a distal end 205, and has an elongated geometry with a round cross-section configured to fit within the recess of the cup 104 as shown in the preferred embodiment shown in FIG. 2. The post 202 defines a post axis 206 that extends along the center of round cross-section formed by the post 202. In an example, the external surface of the round cross-section is smooth forming a post 202 with a cylindrical geometry. In such an example, the post axis 202 extends through the center of the cylindrical geometry. In other examples, the external surface of the round cross-section can be faceted or corrugated.

The post body 102 also defines a set of post teeth 208 that are disposed circumferentially about the post axis 206. The post teeth 208 are configured to mate with a corresponding set of cup teeth on the cup 104 (not shown in FIG. 2) to restrict rotational movement of the cup 104 about the post axis 206 while the cup 104 is mounted on the post 202. The post teeth 208 have a tapered geometry such that each tooth 208 has a distal end that is narrower than its base. The post teeth 208 all extend in a common direction, namely, each tooth 208 extends in a direction that is parallel with the post axis 206 and the direction from the base towards the distal end of each tooth 208 is the same as the direction from the base 204 of the post body 102 towards the distal end 205 of the post 202. In this example, the post teeth 208 are disposed proximate the junction of the base 204 and the post 202, that is, the teeth 208 are disposed proximate the location in which the cylinder forming the post 202 extends from the base 204. Also in this example, the post teeth 208 define a larger diameter than the post 202, that is, a diameter defined by the outer surface of the post teeth 208 collectively is larger than a diameter of the outer surface of the post 202.

In other examples, however, the post teeth 208 can be disposed in other locations, such as proximate the distal end 205 of the post 202 with a diameter that is the same or smaller than the diameter of the post 202.

In an example, the distal end 205 of the post 202 can have a taper 211 to allow easier alignment between the post 202 and the recess of the cup 104. In this example, the post 202 is a cylinder with a smooth outer surface that extends from a distal end of the post teeth 208 to the taper 211.

In the example shown in FIG. 2, the post teeth 208 are defined on the outer surface of a portion of the post body 102 adjacent to a base of post 202. The portion of the post body 102 having the post teeth 208 has a generally round cross-section with the post teeth 208 defined on the radially outward portion of the body 102. In an example, the post teeth 208 have exposed surfaces facing radially outward with respect to the cylindrical axis 206, but there are no radially inward facing surfaces because the area radially inward of the post teeth 208 is made up of solid material. In an example, that portion of the post body 102 on which the post teeth 208 are composed is a polygon wherein each side of the polygon corresponds to one tooth 208. For example, if there are five post teeth 208 in the set of post teeth 208, the portion of the post body 102 defining the post teeth 208 can be a pentagon. In other examples, other geometries can be used, such as a cylinder. The outer surfaces of the post teeth 208 can likewise form a cylinder, polygon or other geometry.

In an example, the post body 102 is composed of a monolithic portion of a rigid material (e.g., metal (e.g., aluminum) or plastic) that defines the base 204, the teeth 208, the portion of material radially inward from the teeth 208 and an inner core of the post 202. A polymetric sleeve can be disposed over the inner core of the post 202 to provide a smooth and low friction outer surface of the post 202. In other examples, the post body 102 can be composed in other ways, such as being entirely monolithic.

FIGS. 3A and 3B are a perspective view and a cross-sectional view, respectively, of an example cup 104. As mentioned above, the cup 104 defines a recess 302 having an elongated geometry with a round cross-section that is configured to mate with the elongated geometry of the post 202. The recess 302 defines a recess axis 304 that extends along the center of round cross-section formed by the recess 302. In an example, the internal surface of the round cross-section is smooth forming a recess 302 with a cylindrical geometry. In such an example, the recess axis 304 extends through the center of the cylindrical geometry. In other examples, the internal surface of the round cross-section can be faceted or corrugated.

The post 202 and the recess 302 can be configured such that the post 202 can slide into the recess 302 and substantial contact is maintained between the outer surface of the post 202 and the inner surface of the recess 302 while the post 202 is fully inserted into the recess 302. In an example, the outer surface of the post 202 and the inner surface of the recess 302 are both smooth cylindrical surfaces such that essentially the entire areas of the surfaces that oppose one another maintain contact. This large contact area restricts the ability of the cup 104 to move in any direction normal to the post axis 206 while the cup 104 is mounted to the post 202. In other words, the cup 104 and the post 202 are configured to allow the cup 104 to translate along the post axis 206 and rotate about the post axis 206 but restricts movement in the other (specifically four) degrees of freedom. Allowing translation along the post axis 206 allows the cup 104 to be slid onto and off of the post 202. Allowing rotation about the post axis 206 allows the cup 104 to be rotated to achieve a desired orientation prior to engaging the teeth of the cup with the teeth 208 of the post body 102 and allows the teeth of the cup to be aligned with the teeth of the post body 102 for engagement therebetween as discussed below. During translation and rotation about the post axis 206, the inner surface of the recess 302 slides along the outer surface of the post 202.

In an example, the post 202 and the recess 302 have elongated cylindrical geometries in which a length of the cylinders is at least the same length as a diameter of the cylinders. In particular examples, the length of the cylinders is at least 1.5 times or at least 2 times the diameter of the cylinders. Such a geometry provides good resistance to movement about the four degrees of freedom other than translation and rotation about the post axis 206. This restriction of movement provides stability for the medical instrument 100 while it is mounted to the post 202 by reducing wobble, for example. In an example, the diameter of the inner surface of the recess 302 is less than 1 mm, or less than 0.5 mm larger than the diameter of the outer surface of the post 202 to enable sufficient contact to be maintained between the opposing surfaces.

Similar to the post axis 206, the recess 302 defines a recess axis 304 that extends along a center of the cylinder formed by the recess 302. When the cup 104 is mated to the post 202, the recess axis 304 is aligned with the post axis 206. The recess 302 defines an inner end 306 and an outer end 308. The post 202 is inserted into the outer end 308 of the recess 302 and slid towards the inner end 306 for full engagement. In this example, the recess 302 has a smooth inner surface corresponding in size to the smooth outer surface of the post 202.

The cup 104 defines a set of cup teeth 310 that are disposed circumferentially about the recess axis 304. The cup teeth 310 are configured to mate with the post teeth 208 of the post body 102. The cup teeth 310 have a tapered geometry such that each tooth 310 has a distal end that is narrower than its base. The cup teeth 310 all extend in a common direction, namely, each tooth 310 extends in a direction that is parallel with the recess axis 304. In particular, the direction from the base towards the distal end of each tooth 310 is the same as the direction from the inner end 306 of the recess 304 towards the outer end 308 of the recess 304. In this example, the cup teeth 310 are disposed proximate the outer end 308 of the recess 304 and an inner surface of the teeth 310 collectively defines a diameter that is the same as or slightly larger than a diameter of the inner surface of the recess 302. The diameter defined by the cup teeth 310 corresponds to the diameter defined by the post teeth 208 enabling the two sets of teeth 208, 310 to engage when the cup 104 and post body 102 are mounted. When the post 202 is fully inserted into the recess 304, the cup teeth 310 engage with the post teeth 208 to restrict rotation about the post axis 206. Thus, the user is allowed to rotate the medical instrument 100 while the post 202 is partially inserted into the recess 304 to achieve an approximate desired orientation. Then, the user can slide the recess 304 farther onto the post 202 to engage the cup teeth 310 with the post teeth 208. Upon full engagement of the cup teeth 310 with the post teeth 208, then rotation of the cup 104 about the post axis 206 is restricted thereby stabilizing the medical instrument 100 in its desired orientation. If the post teeth 208 are disposed in other locations on the post body 102 (e.g., proximate the distal end 205 of the post 202), then the cup teeth 310 would be correspondingly disposed (e.g., proximate the inner end of the recess 302 and having a diameter smaller than the internal diameter of the recess 302).

Also in this example, the cup teeth 310 protrude from the outer end 308 of the recess 302. In other examples, the cup teeth 310 can be defined on the internal surface of a portion of material having a generally round inner geometry. That is, the area radially outward from the cup teeth 310 is composed of material (e.g., plastic or metal) whereby the portion of the cup 104 radially outward from the cup teeth 310 and the cup teeth 310 themselves are a monolithic section of material, with the cup teeth 310 defined on the radially inward portion of the material. In an example, the cup teeth 310 are composed in a polygon geometry wherein each side of the polygon corresponds to one tooth 310. For example, if there are five cup teeth 310 in the set of cup teeth 310, the cup teeth 310 can form a pentagon. In other examples, other geometries can be used, such as a cylinder. The outer surfaces of the cup teeth 310 can likewise form a cylinder, polygon or other geometry.

FIG. 4 is a perspective view of an example set of teeth 400, which can be used for post teeth 208 and cup teeth 310. In an example, the set of teeth 400 includes at least three teeth 402. Preferably, the set of teeth 400 includes from three to nine teeth 402. The teeth 402 all extend in a common direction and are disposed generally about a circumferential path. As described above, a center of the circular disposition formed by the teeth 402 is aligned with the post axis 206 or recess axis 304 such that the teeth 402 are disposed circumferentially about their respective axes 206, 304. A representative teeth axis 403 is shown in FIG. 4, which would correspond to the post axis 206 or recess axis 304 respectively. Each tooth has a base 404 and a distal end 406 and is tapered such that the distal end 406 has an extension that is narrower than the extension of the base 404. Each tooth 402 has two lateral edges 408 that define respective gaps 410 between adjacent teeth 408 and are angled towards each other forming the taper of each tooth 410. The angle of each lateral edge 408 is less than 30 degrees off of parallel with the teeth axis 403, preferably less than 15 degrees off of parallel with the teeth axis 403. In a specific example, each lateral edge 408 has an angle 412 of about 7 degrees off of parallel with the teeth axis 403.

Figure 5:
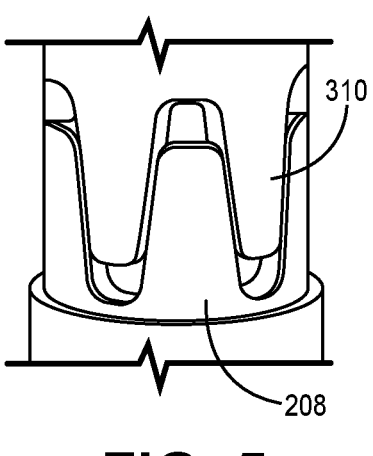
FIG. 5 is an enlarged perspective view of example teeth from the post body of FIG. 2 engaged with teeth of the cup of FIGS. 3A and 3B.

FIG. 5 is a perspective view of the post teeth 208 in a fully engaged position with the cup teeth 310. To engage the post teeth 208 and the cup teeth 310, the teeth 402 from each set 208, 310 are inserted into the gaps 410 between teeth 402 of the opposing set 310, 208. During engagement the lateral edges 408 of the teeth 402 contact the lateral edges 408 of the opposing set of teeth 310, 208. The sets of teeth 208, 310 (as well as the cup 104 and post 202 more generally) are fully engaged when the contact between the lateral edges 408 prevents further movement of the sets of teeth 208, 310 towards one another. The contact between the lateral edges 408 of the opposing teeth 402 restricts rotation of the cup 104 about the teeth axis 403 (i.e., the post axis 206). The teeth 402 of both sets of teeth 208, 310 can have lateral edges disposed at the same angle (e.g., about 7 degrees from parallel with the teeth axis 403) to provide a large area of contact between the opposing lateral edges 408. The overall size of each tooth 402 also corresponds to the size of the gap 410 in the opposing set of teeth 208, 310 in which that tooth 402 is to be inserted such that both lateral edges 408 of each tooth 402 maintain contact with lateral edges 408 of teeth 402 in the opposing set 208, 310. In the example shown in FIG. 5, each tooth 402 in both sets of teeth 208, 310 has a common geometry and each gap 410 in both sets of teeth 208, 310 has a corresponding common geometry such that any tooth 402 from the set of post teeth 208 will fit into any gap 410 in the set of cup teeth 310 and vice versa. In this configuration, each tooth is disposed equally about the circumferential path to allow for opposing teeth to be lined up and engaged without having to rotate the cup or post a substantial amount by the user in order to properly install the medical instrument 100 in its operating position. For example, if using five teeth as shown in FIG. 5, at most 72 degrees of rotation would at most be needed to mate the opposing set of teeth 208, 310. Preferably, there are an odd number of teeth in each set of teeth 208, 310 to provide balanced force distribution about the circle. In an example, the lateral edges 408 of each tooth 402 are flat such that the contact between the lateral edges 408 is between two flat surfaces.

Each tooth 402 is blunt at its distal end 406 such that the distal end 406 remains spaced apart from a bottom of the gap 410 it is engaged in when the sets of teeth 208, 310 are in their fully engaged positions. Keeping the distal end 406 spaced apart from the bottom of the gap 410 directs the contact between opposing sets of teeth to be between the opposing lateral edges 408 as discussed above. In order to provide such a space between the teeth 402 and the bottom of the gap 410, each tooth 402 is sufficiently blunt such that the distal end 406 of each tooth 402 is wider than the bottom of the gap 410.

Figure 6:
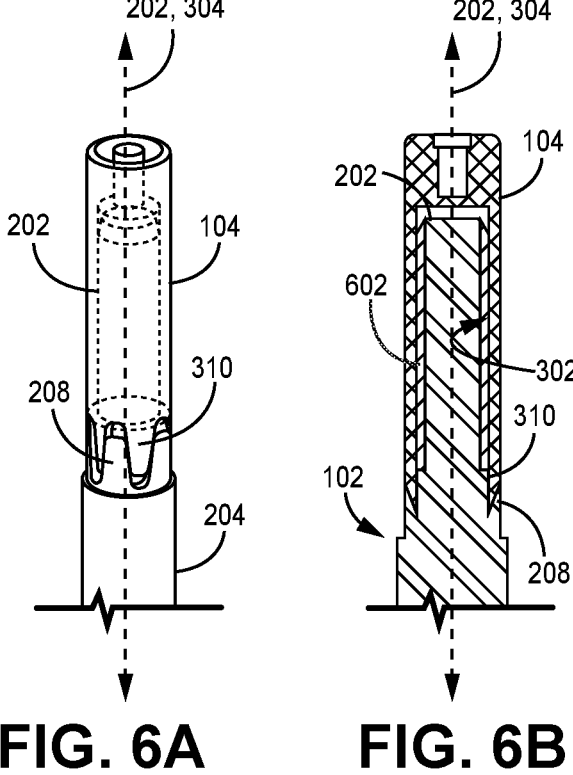
FIG. 6A is perspective view of the example cup of FIGS. 3A and 3B mounted to the post body of FIG. 2.
FIG. 6B is a cross-sectional view of the example cup of FIGS. 3A and 3B mounted to the post body of FIG. 2.

FIGS. 6A and 6B are a perspective and a cross-sectional view of the cup 104 in a fully engaged position with the post body 102. In the fully engaged position, the lateral edges of the teeth 310 of the cup 104 are in contact with the lateral edges of teeth 208 of the post body 102. Additionally, the inner surface of the recess 302 of the cup 104 is in contact with the outer surface of the post 202. In this example, the post 202 includes a sleeve 602 that defines the outer surface of the post 202, such that the outer surface of the sleeve 602 contacts the inner surface of the recess 302. These contacting surfaces collectively provide stability for the medical instrument 100 by restricting movement of the cup 104 in five of the six degrees of freedom. Thus, a user can simply slide the medical instrument 100 onto the post body 102, engaging the teeth 310 of the cup 104 with the teeth 208 of the post body 102, and release the medical instrument 100. The cup 104 and post body 102 hold the medical instrument 100 stable after the user releases the instrument 100. By orienting the post 202 in a vertical direction, the cup 104 and post body 102 utilize gravity to maintain engagement between the teeth 310 of the cup 104 and the teeth 208 of the post body 102. The one degree of freedom that is not restricted is translation along the post axis 206. Translation along the post axis 206 allows the medical instrument 100 to be removed from the post body 102 by lifting the medical instrument 100 thereby disengaging the teeth 310 of the cup 104 from the teeth 208 of the post body 102 and sliding the cup 104 off of the post 202. In this example, no tools are required to mount or dismount the medical device 100.

Referring back to FIG. 4 along with FIGS. 6A and 6B, the dimensions of the teeth 402 including their height (distance between base and distal end), width, and the angle of the lateral edges 408 can be selected based on the weight which the quick connect mechanism 101 is to bear, e.g., the weight of the medical instrument 100 along with any other weight applied during use. The dimensions of the teeth 402 can also be selected based on the use of the medical instrument 100. For example, a longer lateral edge 408 with a shallower angle can provide more binding between the sets of teeth 208, 310. More binding may be desirable for implementations in which the quick connect mechanism is to bear lower weight, because it will provide the additional resistance to rotation or other movement of the cup 104 relative to the post body 102. However, less binding may be desirable for implementations in which the quick connect mechanism is to bear a higher weight, because it will allow the teeth 310 of the cup 104 to be more easily disengaged with the teeth 208 of the post body 102. The dimensions of the post 202 and recess 302 can be similarly selected based on the medical instrument 100 and the expected use thereof.

In an example, the medical instrument 100 is approximately 20-25 pounds (9-11 kg), the post 202 is about 50-70 mm long and about 14-18 mm in diameter. The post teeth 208 and cup teeth 310 consist of 5 teeth each, each tooth is about 12-18 mm in height with lateral edges oriented at about 6-8 degrees. All teeth in the post teeth 208 and the cup teeth 310 are the same size, are evenly spaced and the gaps between adjacent teeth are also the same size as one another and have the same dimension as the teeth 208, 310. The diameter of the outer surface of the post teeth 208 is about 22-27 mm. The inner diameter of the recess 302 is about 14-18 mm and there is about 0.1-0.3 mm difference between the inner diameter of the recess 302 and the outer diameter of the post 202. The inner cylinder of the recess 302 is about 50-70 mm in length.

In an example, the outer surface of the post 202 and the inner surface of the recess 302 are composed of materials that have a low coefficient of friction with one another to allow easier sliding of the recess 302 on the post 202. For example, the outer surface of the post 202 and/or the inner surface of the recess 302 can be composed of Acetal, PEEK, UHMW Polyethylene, acrylic or other plastics with a low coefficient of friction. The longitudinal geometry of the recess 302 can be sufficiently long such that the transverse surface at the distal end of the post 202 does not contact the cup 104, thereby allowing full engagement between the teeth 310 of the cup 104 and the teeth 208 of the post body 102.

Figure 7:
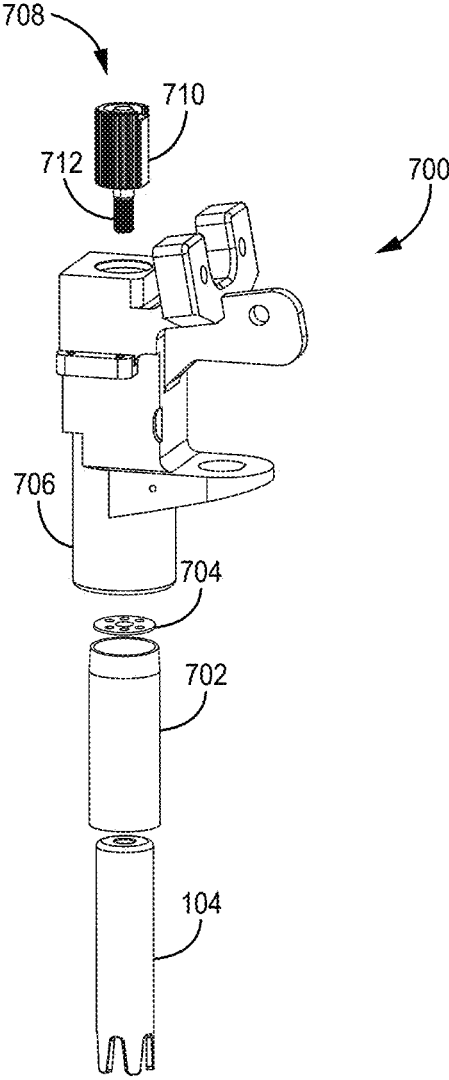
FIG. 7 is an exploded view of an example assembly for providing controlled torque to the medical instrument of FIG. 1 when used in conjunction with the quick connect mechanism of FIG. 1.

FIG. 7 is an exploded view of an example assembly 700 that enables a medical instrument 100 to be controllably rotated about the recess axis 304 while mounted to a post body 102. The assembly 700 includes a cup 104 as described above along with a sleeve 702, a thrust bearing 704, a medical instrument mount 706, and a torque controller 708. The sleeve 702 is configured to be pressed onto or otherwise fixed to the cup 104 such that once they are pressed together the sleeve 702 does not move relative to the cup 104. The sleeve 702 defines a cylindrical outer surface having a diameter that corresponds to a diameter of an inner surface of a recess defined in the medical instrument mount 706. The recess of the medical instrument mount 706 is configured to fit over the sleeve 702 and to rotate about the recess axis 304 relative to the sleeve 702 so that the medical instrument can be rotatably operated by the user. During rotation of the medical instrument mount 706 relative to the sleeve 702, the inner surface of the recess of the medical instrument mount 706 slides against the outer surface of the sleeve 702. The outer surface of the sleeve 702 and/or the inner surface of the recess of the medical instrument mount 706 can be smooth and of low friction enabling the medical instrument mount 706 to rotate easily with respect to the sleeve 702

An inner shoulder of recess of the medical instrument mount 706 can bear on an upper surface of the sleeve 702 with the thrust bearing 704 (e.g., a washer) disposed therebetween to facilitate low friction sliding between the bearing surfaces. The medical instrument mount 706 can have any suitable shape for attachment to a medical instrument. In an example, the medical instrument mount 706 can be configured to be fastened to a medical instrument with appropriate fasteners such as bolts. In an alternative example, the medical instrument mount 706 can be a monolithic part of a body of the medical instrument.

The torque controller 708 can be a commercial off the shelf component that controls the rotation between the medical instrument mount 706 and the sleeve 702 based on torque. The torque controller can be mounted in the medical instrument such that a body 710 of the torque controller 708 is in a fixed relationship with (i.e., does not move relative to) the medical instrument mount 706. The torque controller 708 can have an arm 712 that extends through an aperture in the medical instrument mount 706 and engages with the sleeve 702 and/or the cup 104. The arm 712 is in a fixed relationship with (i.e., does not move relative to) the sleeve 702 and cup 104. Any suitable mechanism can be used to mount the body 710 and the arm 712 of the torque controller 708 in a fixed relationship with the medical instrument mount 706 and the cup 104/sleeve 702 respectively such as appropriate notches defined in opposing surfaces between the body 710 and medical instrument mount 706 and between the arm 712 and an aperture in the cup 104/sleeve 702. The torque controller 708 can control rotation between the medical instrument mount 706 and the sleeve 702/cup 104 by controlling the torque between its body 710 and its arm 712. The torque controller 706 can define a torque axis about which the arm 712 rotates relative to the body 710. The torque controller 706 can be disposed such that the torque axis is aligned with the recess axis 304 of the cup 104. Such a design used along with the quick connect mechanism allows the medical instrument 100 to be rotated with a controlled torque in a manner that is predictable to the user because the axis of rotation is aligned with the recess and post axes 304, 206 while the medical instrument 100 is mounted to the post body 102. The torque parameters of the torque controller 706 can be selected based on the weight, size, and intended use of the medical instrument 100.

The medical instrument 100 can be any suitable instrument used in a medical setting such as an injector head, a medical device control panel or console or use interface, a tray, a computer, a display or monitor, or a medical device in general. Although the quick connect mechanism has been described herein as having the post body 102 on the bottom and mounted to a fixture and the cup 104 being part of the medical instrument 100, in an alternative example, the cup 104 is on the bottom mounted to a fixture and the post body 102 in integrated into the medical instrument 100. Such an alternative example would function in essentially the same manner with the medical instrument 100 being maneuvered to align the post 202 of the post body 102 with the recess 302 of the cup 104 and then lowering the post 202 into the recess 302 to ultimately engage the teeth 208 of the post body 102 with the teeth 310 of the cup 104.

What is claimed is:

1. A quick connect mechanism of a medical instrument, the mechanism comprising:
   a post body including:
      a base;
      a post extending from the base and having an elongated geometry with a round cross-section that defines a post axis about its center, the post having a distal end; and
      a set of post teeth disposed circumferentially about the post axis, the base having a diameter greater than a diameter of an outer surface of the set of post teeth, each tooth in the set of post teeth extending in parallel with the post axis towards the distal end of the post, each tooth in the set of post teeth having lateral edges that define gaps between adjacent teeth, the lateral edges angled relative to the post axis such that a distal end of each tooth is narrower than a base of the tooth, the distal end of the post extending beyond the distal end of each post tooth;
   a cup defining:
      a recess having an elongated geometry with a round cross-section that defines a recess axis about its center, the recess having an inner end and an outer end; and
      a set of cup teeth disposed circumferentially about the recess axis, each tooth in the set of cup teeth extending in parallel with the recess axis, each tooth in the set of cup teeth having lateral edges that define gaps between adjacent teeth, the lateral edges angled relative to the recess axis such that a distal end of each tooth is narrower than a base of the tooth,
   wherein one of the post body or the cup is configured to be mounted such that the post axis or recess axis respectively is disposed vertically and the other of the post body or cup is disposed on the medical instrument,
   wherein the recess is configured to mate with the post such that the post axis is aligned with the recess axis and an outer surface of the post maintains contact with an inner surface of the recess in order to mount the medical instrument to the post body,
   wherein the set of cup teeth are configured to mate with the set of post teeth in order to restrict rotation of the cup relative to the post about the recess axis.

2. The quick connect mechanism of claim 1, wherein the set of post teeth and the set of cup teeth have dimensions such that the lateral edges of the set of post teeth maintain contact with the lateral edges of the set of cup teeth while mated.

3. The quick connect mechanism of claim 2, wherein the lateral edges of the set of post teeth are angled relative to the post axis in the same manner as the lateral edges of the set of cup teeth are angled relative to the recess axis to provide an elongated contact surface between the lateral edges of the set of post teeth and the lateral edges of the set of cup teeth.

4. The quick connect mechanism of claim 3, wherein the distal ends of the post teeth are spaced apart from the gaps between the cup teeth, and the distal ends of the cup teeth are spaced apart from the gaps between the post teeth while mated.

5. The quick connect mechanism of claim 1, wherein the post has a length that is at least 1.5 times longer than its diameter and the recess has a length that is at least 1.5 times longer than its diameter.

6. The quick connect mechanism of claim 5, wherein the outer surface of the post is smooth and the inner surface of the recess is smooth to allow the outer surface of the post to slide against the inner surface of the recess during insertion of the post into the recess.

7. The quick connect mechanism of claim 6, wherein the set of post teeth are disposed proximate an intersection of the post and the base, and the set of cup teeth are disposed proximate the outer end of the recess.

8. The quick connect mechanism of claim 1, wherein the set of post teeth and the set of cup teeth each include at least three teeth.

9. The quick connect mechanism of claim 1, wherein the lateral edges of the set of post teeth are angled less than 30 degrees off the post axis, and the lateral edges of the set of cup teeth are angled less than 30 degrees off the recess axis.

10. The quick connect mechanism of claim 1, wherein a diameter defined by the inner surface of the recess is less than 1 mm larger than a diameter defined by the outer surface of the post.

11. The quick connect mechanism of claim 1, comprising:

a sleeve fixed about an exterior of the cup, the sleeve defining a cylindrical outer surface that is configured to slide against an inner surface of a recess of the medical instrument, enabling rotation of the sleeve, cup, and post body about the recess axis relative to the medical instrument; and a bearing disposed between an end of the cup proximate the inner end of the recess and the medical instrument to reduce friction between the medical instrument and at least one of the cup and sleeve during rotation of the sleeve, cup, and post body relative to the medical instrument.

12. The quick connect mechanism of claim 11, comprising:

a torque controller having a body and an arm, and being configured to control rotation of the arm relative to the body about a torque axis, wherein the body of the torque controller is mounted to the medical instrument in a fixed relationship, and the arm of the torque controller is mounted to the cup in a fixed relationship, wherein the torque axis is aligned with the recess axis of the cup.

13. A quick connect mechanism of a medical instrument, the mechanism comprising:

a post body including:

a base;

a post extending from the base and having an outer surface that is smooth and forms a cylinder, the post defining a post cylindrical axis about a center of the cylinder, the post having a distal end; and a set of post teeth disposed proximate an intersection of the post and the base and disposed circumferentially about the post cylindrical axis, wherein an outer surface of the set of post teeth defines a diameter that is larger than a diameter of the cylinder formed by the outer surface of the post, wherein the base defines a diameter greater than a diameter of the outer surface of the set of post teeth, each tooth in the set of post teeth extending in parallel with the post cylindrical axis towards the distal end of the post, each tooth in the set of post teeth having lateral edges that define gaps between adjacent teeth, the lateral edges angled relative to the post cylindrical axis such that a distal end of each tooth is narrower than a base of the tooth, the distal end of the post extending beyond the distal end of each post tooth;

a cup defining:

a recess having an inner surface that is smooth and forms a cylinder, the recess defining a recess cylindrical axis about a center of the cylinder, the recess having an inner end and an outer end; and a set of cup teeth extending from the outer end of the recess and disposed circumferentially about the recess cylindrical axis, wherein an inner surface of the set of cup teeth defines a diameter that is larger than the diameter of the cylinder formed by the outer surface of the post and smaller than the diameter formed by the outer surface of the set of post teeth, each tooth in the set of cup teeth extending in parallel with the recess cylindrical axis away from the outer end of the recess, each tooth in the set of cup teeth having lateral edges that define gaps between adjacent teeth, the lateral edges angled relative to the recess cylindrical axis such that a distal end of each tooth is narrower than a base of the tooth, wherein the post body is configured to be mounted such that the post cylindrical axis is disposed vertically, wherein the cup is disposed on a medical instrument, wherein the recess is configured to mate with the post such that the post cylindrical axis is aligned with the recess cylindrical axis and the outer surface of the post maintains contact with the inner surface of the recess in order to mount the medical instrument to the post body, wherein the set of cup teeth are configured to mate with the set of post teeth in order to restrict rotation of the cup relative to the post about the post cylindrical axis.

14. The quick connect mechanism of claim 13, wherein the set of post teeth and the set of cup teeth have dimensions such that the lateral edges of the set of post teeth maintain contact with the lateral edges of the set of cup teeth while mated.

15. The quick connect mechanism of claim 14, wherein the lateral edges of the set of post teeth are angled relative to the post cylindrical axis in the same manner as the lateral edges of the set of cup teeth are angled relative to the recess cylindrical axis to provide an elongated contact surface between the lateral edges of the set of post teeth and the lateral edges of the set of cup teeth.

16. The quick connect mechanism of claim 15, wherein the distal ends of the post teeth are spaced apart from the gaps between the cup teeth, and the distal ends of the cup teeth are spaced apart from the gaps between the post teeth while mated.

17. The quick connect mechanism of claim 13, wherein the post has a length that is at least 1.5 times longer than its diameter and the recess has a length that is at least 1.5 times longer than its diameter.

18. The quick connect mechanism of claim 13, wherein a diameter defined by the inner surface of the recess is less than 1 mm larger than a diameter defined by the outer surface of the post.

19. The quick connect mechanism of claim 13, wherein the set of post teeth and the set of cup teeth each include at least three teeth.

20. The quick connect mechanism of claim 13, wherein the lateral edges of the set of post teeth are angled less than 15 degrees off the post cylindrical axis and the lateral edges of the set of cup teeth are angled less than 15 degrees off the recess cylindrical axis.

21. The quick connect mechanism of claim 13, comprising:

a sleeve fixed about an exterior of the cup, the sleeve defining a cylindrical outer surface that is configured to slide against an inner surface of a recess of the medical instrument, enabling rotation of the sleeve, cup, and post body about the recess cylindrical axis relative to the medical instrument; and a bearing disposed between an end of the cup proximate the inner end of the recess and the medical instrument to reduce friction between the medical instrument and at least one of the cup and sleeve during rotation of the sleeve, cup, and post body relative to the medical instrument.

22. The quick connect mechanism of claim 21, comprising:

a torque controller having a body and an arm and being configured to control rotation of the arm relative to the body about a torque axis, wherein the body of the torque controller is mounted to the medical instrument in a fixed relationship, and the arm of the torque controller is mounted to the cup in a fixed relationship, wherein the torque axis is aligned with the recess cylindrical axis.

* * * * *